United States Patent [19]

Chestnut

[11] Patent Number: 4,815,467
[45] Date of Patent: Mar. 28, 1989

[54] ACROMIOPLASTY GUIDE PINS

[76] Inventor: William J. Chestnut, 2526 El Fego Rd., N.W., Albuquerque, N. Mex. 87197

[21] Appl. No.: 25,424

[22] Filed: Mar. 13, 1987

[51] Int. Cl.$^4$ ............................................. A61B 17/34
[52] U.S. Cl. ............................. 128/329 R; 128/303 R
[58] Field of Search ........... 128/303 B, 303 R, 329 A, 128/329 R, 737, 907, 92 R, 92 Z, 92 VD, 92 V, 92 VL

[56] References Cited

U.S. PATENT DOCUMENTS

| | | | |
|---|---|---|---|
| 1,248,340 | 11/1917 | Kinney . | |
| 1,960,892 | 5/1934 | Boever | 128/92 Z |
| 3,039,468 | 1/1962 | Price | 128/329 |
| 3,053,256 | 9/1962 | Cooper et al. . | |
| 3,357,431 | 12/1967 | Newell | 128/303 B |
| 3,410,269 | 11/1968 | Hovick | 128/329 |
| 3,916,529 | 11/1975 | Mousseau . | |
| 3,964,480 | 1/1970 | Froning | 128/303 B |
| 4,005,527 | 2/1977 | Wilson et al. . | |
| 4,058,114 | 11/1977 | Soldner | 128/303 B |
| 4,349,018 | 9/1982 | Chambers . | |
| 4,421,112 | 12/1983 | Mains et al. . | |
| 4,471,780 | 9/1984 | Menges et al. | 128/326 |
| 4,545,373 | 10/1985 | Christoudias | 128/303 R |

FOREIGN PATENT DOCUMENTS 0643146  1/1979  U.S.S.R. .............................. 128/737

OTHER PUBLICATIONS

"Device For Determining The Location of A foregion Body", English translation of USSR 643,146 to Yurchak et al.

Primary Examiner—Max Hindenburg
Attorney, Agent, or Firm—Nilsson, Robbins, Berliner, Carson & Wurst

[57] ABSTRACT

A surgical device primarily useful in arthroscopic acromioplasty surgery, the device, typically a pin, is formed to be temporarily implantable and fixable at a desired depth in one or more locations of the shoulder region. By the proper positioning of one or more of these pins a surgeon can visually identify the various shoulder anatomy, e.g., the acromion, the acromioclavicular joint, the clavicle and the associated ligaments and muscles, to determine the appropriate portion of the acromion to be resected. This allows the surgeon to avoid injuring the various ligments positioned contiguous to the acromior. The surgical device may also be formed with a visually observable measurement scale that can be positioned adjacent to that area of the acromion which is being resected to allow the surgeon to visually determine the extent of the resection.

20 Claims, 2 Drawing Sheets

ACROMIOPLASTY GUIDE PINS

BACKGROUND OF THE INVENTION

The invention is directed to surgical instruments, specifically, surgical pins used to indicate the location of the various parts of the human shoulder anatomy while arthroscopic acromioplasty is being performed.

Arthroscopic acromioplasty is performed to relieve the symptoms of chronic bursitis of the shoulder. Generally, chronic bursitis may occur as a result of the acromion process of the scapula impinging upon the underlying rotator muscles and associated ligaments. This impingement may be the result of an injury to the shoulder or the result of bone spurs formed on the acromion which impinge upon the rotator muscles and associated ligaments, or bone spurs formed in the acromioclavicular joint, either on the clavicle or the acromion, which would direct the acromion to impinge against the rotator muscles and associated ligaments.

There are various approaches to treat shoulder bursitis depending upon the severity of the inflammation. These treatments include specific types of exercise developed to relieve the inflammation and also include the use of medication. However, certain cases of shoulder bursitis can not be relieved by the use of these nondestructive techniques and the only recourse would be surgery.

Generally, the surgical technique performed on the shoulder to alleviate the suffering caused by the bursitis involves the resection of the underlying area of the acromion, that is, the underlying anterior and posterior portion of the acromion, which impinges upon the rotator muscles and associated ligaments. It may also be necessary to surgically remove any bone spurs found on the acromion or clavicle, or to excise a portion of the coracoacromial ligmant.

While this surgery may be performed as an open surgical procedure, the more typical approach is to perform arthoscopic surgery, more specifically, arthroscopic acromioplasty. Arthroscopic surgery reduces the damage which typically occurs with open surgical procedures, e.g., morbidity, and promotes earlier rehabilitation.

The major drawback with arthoscopic surgery, and in particular arthoscopic acromioplasty, is the difficulty in visually observing and distinguishing between the various bones and ligaments of the shoulder anatomy. It is further difficult to precisely ascertain the location of the acromion at which the resection is to be performed and to determine with any degree of accuracy the extent of the resection.

Typically, the surgeon will mark the patient's skin about the shoulder to provide the general location of the underlying acromion, clavicle, acromioclavicular joint and other structures of the shoulder. The surgeon will then refer to these markings during the operation and estimate which part of the shoulder anatomy he is observing through the arthroscope and the location of the acromion to be resected.

While a skilled surgeon may adequately perform the arthroscopic acromioplasty using these exterior markings as reference points, there exists the possibility that the wrong area of the acromion will be resected, or more probably that the estimated extent of the resection will be either too low, or more dangerous, too high. The extent of the resection is usually visually estimated by comparing the depth of the resection to the surrounding facie. However, even under the most favorable conditions the surgeon must still estimate both the location of the acromion to be resected and the extent of the resection.

It is thus apparent that any improvement in the ability to visually observe both the precise identity of the various parts of the shoulder anatomy, the location of that area of the acromion to be resected and the extent of the resection, would be an improvement over the current procedure.

SUMMARY OF THE INVENTION

The present invention achieves the above objectives by providing a surgical device, typically a pin, which is temporarily implantable and fixable at a desirable depth in one or more locations of the shoulder region. By the proper positioning of one or more of these pins the surgeon can visually identify the various shoulder anatomy, e.g., the acromion, the acromioclavicular joint, the clavicle and the associated ligaments and muscles, and determine the position of the acromion to be resected. This allows the surgeon to avoid injuring the various ligaments positioned contiguous to the acromion.

Furthermore, the surgical device of the invention is formed with a visually observable measurement scale that can be positioned adjacent to that area of the acromion, or other bone, which is to be resected. This allows the surgeon to visually determine the extent of the resection.

BRIEF DESCRIPTION OF THE FIGURES

The present invention will be better understood, and its various objectives and advantages will be apparent to those skilled in the art by reference to the following figures, wherein like reference numerals refer to like elements in the several figures and wherein.

DETAILED DESCRIPTION OF THE INVENTION

The present invention is directed to a surgical device, e.g. a pin, which is temporarily implantable and fixable at a depth in the shoulder area to allow visual identification of the internal shoulder anatomy during arthoscopic acromioplasty. By fixing the device at a given depth in the shoulder and by forming a measurement scale on its outer surface, the device functions as a reference of measurement allowing the visual observation of the extent of the reaction.

While the present invention will be described in its use with arthroscopic acromioplasty surgery, it is not to be so limited. That is, the surgical device of the invention may be utilized in any type of operation where visual observation of the internal anatomy is necessary and because of the manner by which the operation is performed such visual observation is limited, such as any non-open surgical procedure. More specifically, the surgical device of the invention may be utilized in any of the various arthroscopic procedures performed on the shoulder and knees.

The surgical device of the invention is particularly useful in arthroscopic acromioplasty surgery because of the need to distinguish between the various shoulder anatomy and to determine the location of the acromion at which to operate, that is, resect. This visual observation allows the surgeon to avoid damaging nearby tissue. Furthermore, during this operation the surgeon must determine the extent of the resection of the acromion. As stated earlier, the present operating procedure requires the surgeon to visually estimate the extent of the resection. This may lead to the surgeon erring on the side of not enough resection or possibly resecting too much of the bone with the resulting consequences. In accordance with a preferred embodiment of the invention, the surgical device is formd along its surface with a visually observable measurement scale to which the surgeon can refer during the resecting.

Figure 1:
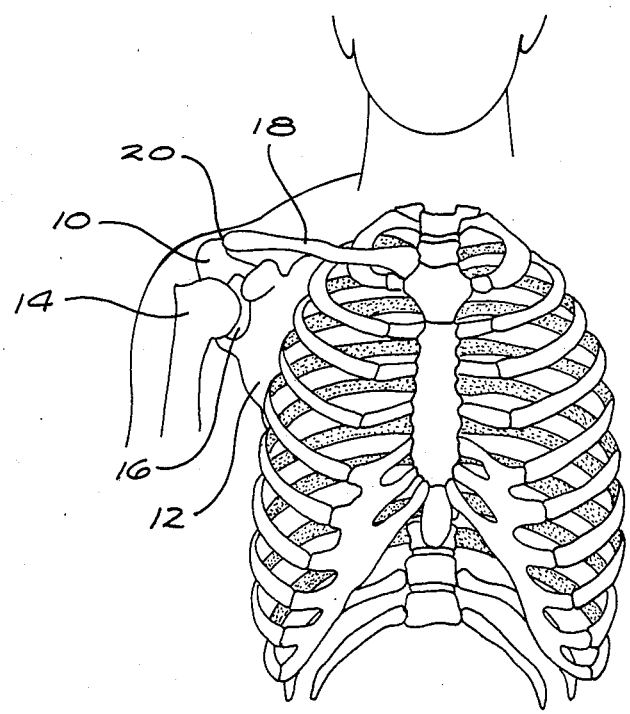
FIG. 1 is a schematic illustration of the anterior shoulder anatomy.

Briefly, arthroscopic acromioplasty surgery involves the resection of the underlying area of the acromion to reduce the degree to which the acromion impinges upon the underlying tissue, namely the bursae and the shoulder rotator cup muscle. As seen in FIG. 1, the acromion 10 is a process on the scapula 12, with the acromion process 10 positioned above the humerus 14. The scapula 12 possesses a glenoid cavity 16, which in conjunction with the head of the humerus 14 forms the shoulder joint. The acromion process 10 lies adjacent to and above the humerus head 14. When the shoulder is injured the acromion process 10 may be forced against the underlying facie, e.g., the bursae and rotator cup muscle. The acromion process 10 may also develop bone spurs which may impinge against this underlying tissue, or these spurs may form either on the acromion or the clavicle 18 in the acromioclavicular joint 20 which forces the acromion 10 to impinge against this underlying tissue.

The object of the arthroscopic acromioplasty surgery is to alleviate this impingement by removing an underlying portion of the acromion and/or removing the bone spurs. Generally, the surgeon enters the shoulder area with an arthroscope to locate the injured portion of the bursae and rotator cup muscle, as well as to locate the abrading surface of the acromion 10. At this point the surgeon can, if necessary, remove the injured portion of the rotator cup muscle and bursae, but more than likely will resect that portion of the acromion 10 causing the injury. This resection involves using a power burr to grind away the acromion 10. At present this operation involves estimating the position of the anatomy being observed and resected using at most externally provided markings which indicate the approximate position of the acromion 10 and related anatomy.

Furthermore, at present the extent of the resection is usually estimated by comparing the resected area with the depth of the surrounding tissue and estimating the extent of bone removal. This at best would allow the surgeon to avoid removing too much of the acromion.

As will be described in more detail herein, the surgical device, which is seen generally as a cylindrical shaped pin at 22 in FIGS. 2A and 2B, functions as a reference to allow the surgeon to more reliably locate the various parts of the shoulder anatomy and also functions to allow the surgeon to visually measure the extent of the resection.

Figures 2A, 2B:
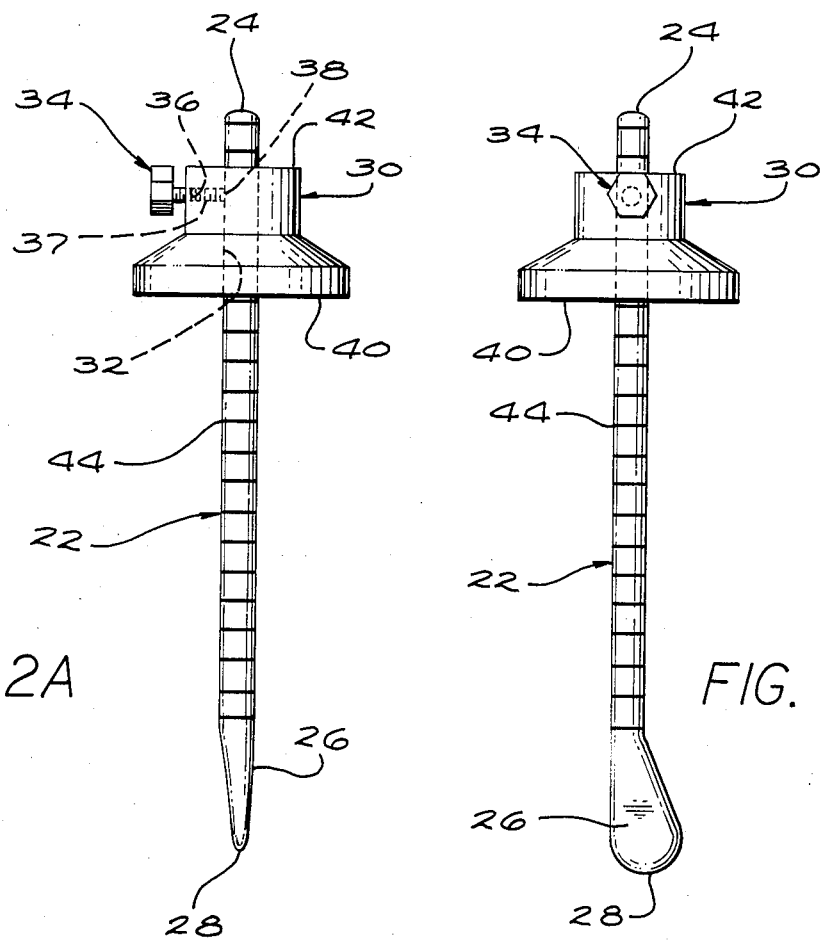
FIG. 2A is a side view of a surgical pin in accordance with an embodiment of the invention.
FIG. 2B is a side view of the surgical pin of FIG. 2A rotated ninety degrees about its axis.

Referring to FIGS. 2A and 2B, the surgical pin 22 is a substantially elongated cylindrical body with a rounded first end 24 and a second opposing end 26, as best seen in FIG. 2B, which end 26 is tapered to form a lowermost edge 28. This edge 28 allows the pin 22 to be easily inserted into the body through a previously made incision; however, this edge 28 should be blunt so as not to cut the skin or muscle itself. This allows the pin 22 to be imbedded in the shoulder without risking any damage to the tissue surrounding the blunt edge 28. The second end 26 is also formed to flare outward, that is, this end 26 is wider than the remaining portion of the pin 22. This wide second end 26 allows a surgeon to more easily locate the pin 22 when the pin 22 is positioned in the shoulder or other area of the body.

The pin 22 should be sufficiently long so that it may be inserted into the desired area of the shoulder or other body area to function as a reference point while allowing a portion thereof to extend out from the body. Generally, the pin 22 may be about eighteen centimeters long and have a diameter of about 4 millimeters. It is that portion of the pin 22 which extends out from the incision to which a collar 30 will be fitted.

The collar 30 is a circular shaped body having two opposing ends 40 and 42, with at least the first of these ends 40 being substantially flat. The collar 30 is formed with a passageway traversing between and exiting at each of the ends 40 and 42, as seen in phantom at 32, through which the pin 22 can pass. This allows the collar 30 to slide along the length of the pin 22.

The collar 30 also includes a set screw 34 having a threaded shank 37 (as seen in phantom in FIG. 2A) which is threadably received in an aperture 36, as seen in FIG. 2A. This aperture 36 lies substantially perpendicular to the passageway 32. The innermost end of the aperture 36 lies in communication with the passageway 32, allowing a first end 38 of the threaded shank 37 of the set screw 34 to enter the passagway 32 when the set screw 34 is threaded into the aperture 36. In this manner the collar 30 can be releasably fixed at a position along the length of the pin 22 by threading the set screw 34 into the aperture 36 until the first end 38 engages and bears against the pin 22. By tightening the first end 38 of the set screw against the pin 22, the pin 22 and the collar 30 can be releasably fixed together.

In accordance with a more preferred embodiment, the surgical pin 22 is formed with a longitudinal measurement scale generally indicated as markings 44. The precise number of the markings 44 formed along the length of the pin 22 will depend upon the length of the pin 22 and the units of measurement to which the markings shall refer by the spacing therebetween. As illustrated, the pin 22 will be about eighteen centimeters long with the markings 44 being separated in increments of millimeters. That is, the distance between each of the individual markings 44 is about one millimeter long.

As will be discussed, this measurement scale as provided by the markings 44 will allow a surgeon to precisely measure the depth of the resection when the pin 22 is positioned contiguous the acromion or other bone being resected, by visually measuring this depth using the scale on pin 22.

While the pin 22 and collar 30 may be constructed from any material which may be sterilized, it is preferable to construct both from stainless steel.

Figure 3:
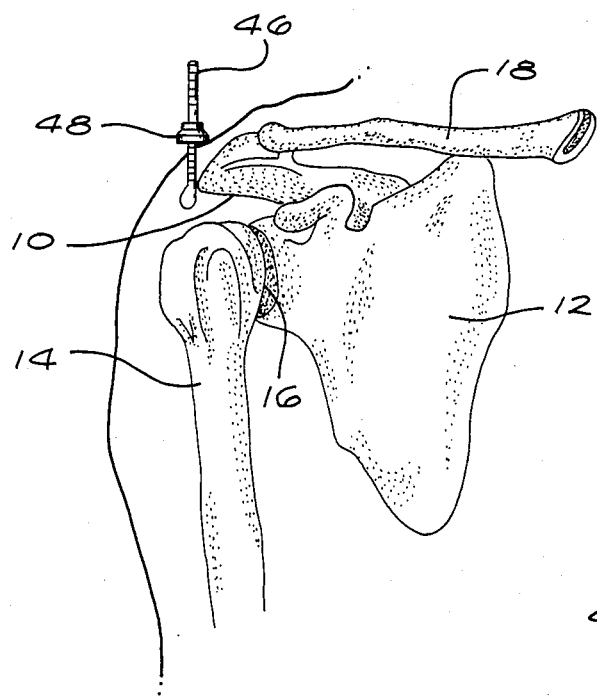
FIGS. 3, 4 and 5 are schematic illustrations of the shoulder anatomy illustrating the placement of one or more of the surgical pins in accordance with a procedure of the invention.
Figure 4:
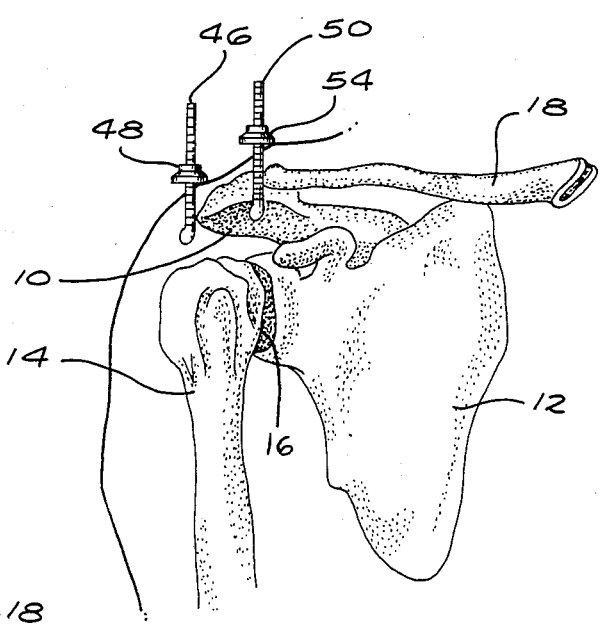
Figure 5:
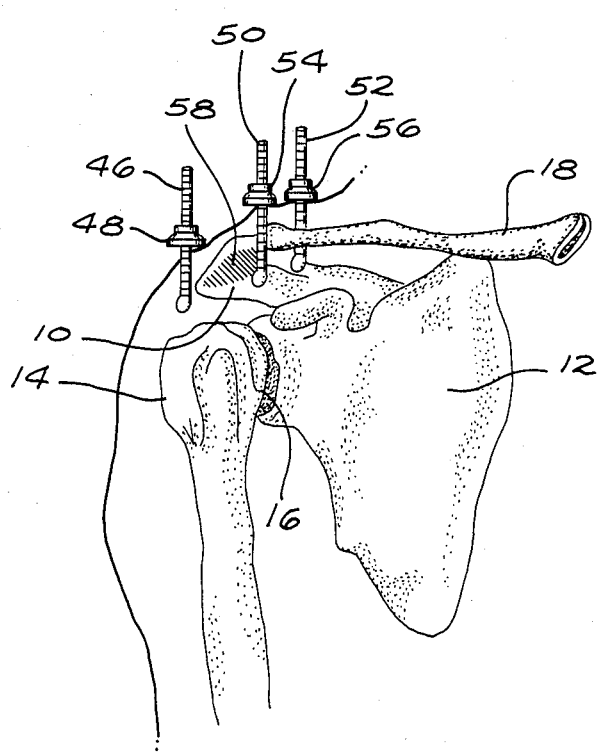

Referring more specifically to FIGS. 3 through 5, the preferred method of using the pin 22 of the invention will be discussed.

As stated, the pin 22 is used to allow a surgeon to visually identify a part of the anatomy of the shoulder during arthroscopic acromioplasty surgery. In accordance with a preferred process of the invention, two or more of the pins 22, more preferably three, are used to function as reference locations. These pins 22 are implanted at known locations in the shoulder to allow visual location of the various bones, joints and ligaments in the shoulder. In order to allow the surgeon to visually distinguish between the various pins 22, each pin 22 is formed to have a distinguishable characteristic. The distinguishing characteristic may be provided by forming each one of the pins 22 from materials of differing colors. Thus by the proper placement of the various pins 22 into the shoulder, the surgeon can visually ascertain his locaion during the operation by observing the color of each of the pins 22.

Thus in accordance with the preferred technique, three pins 22 of different colors will be positioned in the shoulder to reference different bones and ligaments. For example, the three different colors may be gold, blue and silver.

In FIG. 3 the first of the three pins, the gold pin 46, is inserted to lie along the lateral border of the anterior extent of the acromion 10. The manner by which this pin 46 is placed in the shoulder is in conformance with known operating techniques and will not be described herein.

This pin 46 will be positioned at a depth to just touch the rotator cuff muscle which forms the floor of the subacromial space. The positioning of the pin 46 is performed visually using the arthroscope. After the pin 46 is in position, a collar 48 is lowered about the pin 46 and placed against the skin surface of the shoulder through which the pin 46 is inserted and locked at this point to the pin 46 using the inward threading of the respective set screw, not shown. This sets the pin 46 at a fixed depth in the shoulder to insure that it will function properly as a reference point. More important, by setting the pin 46 at this depth, the longitudinally formed measurement scale will be fixed allowing visual measurement of the resection of the acromion. In this regard, the pin 46 should be positioned to allow for visual observation of this measurement scale.

As seen in FIGS. 4 and 5 respectively, two additional pins 50 and 52 are inserted in the shoulder and are fixed at a desired depth by using a respective collar 54 and 56 in the manner as previously discussed. The blue pin 50 is inserted perpendicularly along the anteromedial extent of the acromion 10 anterior of the acromioclavicular joint 20, while the silver pin 52 is positioned posterior to the acromioclavicular joint 20 and the clavicle 18 to reference the acromion 10 in the arthroscopic view.

The acromioplasty procedure is performed after the pins 46, 50 and 52 have been temporarily fixed at desired depths. This typically involves locating the acromion using the pins 46, 50 and 52 as reference points and resecting a sufficient amount from the underside of the acromion to relieve the impingement, with such an area seen generally at 58. This bone resection is performed using a powered burr. The extent of the resection is measured in this case by reference to the measurement scales of either the blue or gold pins, 50 or 46.

After the acromion is sufficiently resected, the coracoacromial ligament can be partially or totally excised. The origin of this ligament is located using the gold and blue pins 46 and 50 which indicate the anterolateral and anteromedial border of the acromion.

Thereafter the acromioclavicular joint is located and examined visually for any bony protuberances which would contribute to the impingement between the acromion and the underlying rotator cuff tendons. This joint is located by the positioning of the blue and silver pins, 50 and 52.

While the preferred embodiments have been described and illustrated, various modification may be made thereto within the scope of the invention. Accordingly, it is to be understood that the invention has been described and illustrated by way of example and not limitation.

What is claimed is:

1. A surgical pin which is implantable through a previously made incision in a body comprising:
    an elongated substantially cylindrical member having a tapered end, said tapered end terminating in a blunt edge so as not to puncture or further damage the skin or muscle of the body in which it is to be implanted;
    said member being formed with a visually observable measurement scale disposed longitudinally along at least a portion of said member; and
    lockable collar means adapted to travel longitudinally along said cylindrical member, and which is further adapted to releasably grip said member at a desired location along said member length, whereby said cylindrical member can be fixed at a desired depth after insertion in said body.

2. The surgical pin of claim 1 wherein said tapered end is formed with a wider cross-sectional dimension than said cylindrical member to allow for easy location of said tapered end when inserted into said body.

3. The surgical pin of claim 1 wherein said measurement scale includes markings which are observable from all longitudinal sides of said elongated member.

4. The surgical pin of claim 3 wherein said measurement scale markings are equally spaced indicia formed about said elongated member portion.

5. The surgical pin of claim 1 wherein said elongated member is further formed with a visually distinguishable characteristic.

6. The surgical pin of claim 5 wherein said visually distinguishable characteristic is a color.

7. The surgical pin of claim 6 wherein said color is placed on at least a portion of said cylindrical member between its midpoint longitudinally and its blunt edge.

8. The surgical pin of claim 1 wherein said locking collar means comprises:
    a member having a passageway formed therethrough, which passageway is dimensioned to receive said cylindrical member; and
    a locking means which is associated with said collar means member and which is operable for engaging a portion of said cylindrical member positioned in said passageway for holding said locking collar member to said cylindrical member.

9. The surgical pin of claim 1 wherein said tapered end flares outward before forming said blunt edge, said flaring occurring in the direction of a plane containing the axis of said cylindrical member.

10. A surgical method for measuring the amount of resection of a portion of one or more bones and/or ligaments in a body by employing a guide pin having a visually observable measurement scale and a lockable collar means which includes the steps of:
    implanting said guide pin at a desired location in said body;

fixing said guide pin at a desired depth at said location by moving said lockable collar means along said guide pin until said collar means engages said body and then operating said collar to releasably grip said guide pin; and resecting said portion of said bone and/or ligament to a desired degree by reference to said measurement scale of said guide pin.

11. The method of claim 10 wherein said guide pin is implanted and fixed at a desired depth along the lateral border of the anterior extent of the acromion.

12. The method of claim 11 wherein a second guide pin is implanted and fixed at a desired depth perpendicularly along the anteromedial extend of the acromion at a position anterior to the acromioclavicular joint.

13. The method of claim 12 wherein a third guide pin is implanted and fixed at a desired depth posterior to the acromioclavicular joint and clavicle.

14. The method of claim 10 further including the step of visually referencing said various bones and/or ligaments in relation to said guide pin after fixing said guide pin at its desired depth and before resecting occurs.

15. The method of claim 14 wherein said visual referencing occurs through the use of an arthroscope.

16. An acromioplasty surgical method for measuring the amount of resection of a portion of one or more bones and/or ligaments forming the human shoulder by employing a guide pin having a visually observable measurement scale and a lockable collar means which includes the steps of:

implanting said guide pin at a desired location in said shoulder;

fixing said guide pin at a desired depth at said location by moving said lockable collar means along said guide pin until said collar means engages said shoulder and then operating said collar to releasably grip said guide pin;

visually referencing the various anatomy of said shoulder during said acromioplasty surgery by a visual reference of said guide pin; and resecting said portion of said bone and/or ligament to a desired degree by reference to said measurement scale of said guide pin.

17. The method of claim 16 wherein said guide pin is implanted and fixed at a desired depth along the lateral border of the anterior extent of the acromion.

18. The method of claim 17 wherein a second guide pin having a distinguishable characteristic different from said first guide pin is implanted and fixed at a desired depth perpendicularly along the anteromedial extent of the acromion at a position anterior to the acromioclavicular joint.

19. The method of claim 18 wherein a third guide pin having a distinguishable characteristic different from said first and second guide pins is implanted and fixed at a desired depth posterior to the acromioclavicular joint and clavicle.

20. The method of claim 16 wherein said visual referencing occurs through the use of an arthroscope.

* * * * *

UNITED STATES PATENT AND TRADEMARK OFFICE
CERTIFICATE OF CORRECTION

PATENT NO. : 4,815,467

DATED : March 28, 1989

INVENTOR(S) : William J. Chesnut

It is certified that error appears in the above-identified patent and that said Letters Patent is hereby corrected as shown below:

Title page:

In the heading the name of the inventor should be changed from "Chestnut" to -- Chesnut --.

On the first page after "Inventor:" the name and address should be changed to -- William J. Chesnut, 2531 Elfego Road N.W., Albuquerque, New Mexico 87107 --.

In the Abstract, line 11 delete "ligments" and insert -- ligaments --.

Column 1, line 37, delete "ligamant" and insert -- ligament --.

Column 2, line 15, delete "desirable" and insert -- desired --.

Column 2, line 42, delete ":" and insert -- ; --.

Column 2, line 60, delete "reaction" and insert -- resection --.

Column 3, line 18, delete "formd" and insert -- formed --.

Column 4, line 37, after "shank 37" insert -- as seen in phantom in FIG. 2A --.

Column 4, line 38, delete "passagway" and insert -- passageway --.

Signed and Sealed this

Twenty-seventh Day of March, 1990

Attest:

JEFFREY M. SAMUELS

Attesting Officer

Acting Commissioner of Patents and Trademarks